United States Patent [19]

Young

[11] Patent Number: 4,620,444
[45] Date of Patent: Nov. 4, 1986

[54] HIGH SPEED GATED PEAK DETECTOR

[75] Inventor: John D. Young, Rexford, N.Y.

[73] Assignee: General Electric Company, Schenectady, N.Y.

[21] Appl. No.: 660,826

[22] Filed: Oct. 15, 1984

[51] Int. Cl.[4] .......................................... G01N 29/04
[52] U.S. Cl. ...................................... 73/606; 73/610; 324/103 P
[58] Field of Search ................. 73/606, 610, 611, 612, 73/602, 620; 324/103 P

[56] References Cited

U.S. PATENT DOCUMENTS 3,783,379   1/1974   Nestorovic ..................... 324/103 P
4,100,808   7/1978   Evans et al. ........................ 73/612
4,233,989   11/1980  Larach et al. ...................... 73/612

OTHER PUBLICATIONS

"Digital and Analog Signal Applications of Operational Amplifiers", J. R. Naylor, pp. 38-46, IEEE *Spectrum*, Jun. 1971.

*Primary Examiner*—Anthony V. Ciarlante
*Attorney, Agent, or Firm*—Donald R. Campbell; James C. Davis, Jr.; Paul R. Webb, II

[57] ABSTRACT

A gated peak detector capable of operating at frequencies of the order of 50 Mhz. and with pulse repetition rates of the order of 10,000 pulses per second includes high speed positive and negative peak detectors driving corresponding sample and hold circuits, the outputs of which are combined in a differential amplifier, the output of which is digitized to provide an output digital signal corresponding to the peak-to-peak value of the input waveform. An automatic polarity selector circuit sums the outputs from the sample and hold circuits, compares the sum to a reference voltage, and controls switches connected to the outputs of the sample and hold circuits and to the input of an analog sample and hold circuit which provides an analog output signal corresponding to the larger of the detected peak values.

20 Claims, 8 Drawing Figures

HIGH SPEED GATED PEAK DETECTOR

BACKGROUND OF THE INVENTION

This invention relates to a new and improved high speed gated peak detector apparatus for detecting and holding the peak amplitude value of a high frequency signal within a preselected time period.

Many signal processing applications have a requirement for peak amplitude detection of RF and pulse waveforms. In the non-destructive ultrasonic inspection and testing of parts, for example, the peak amplitude of a signal reflected from a flaw in the part is proportional to the size of the flaw, and the higher the frequency of the interrogating signal, the smaller the flaw size which can be detected. Sophisticated inspection systems are known which are capable of producing images of flaws. One such system employs a high frequency focused beam scanning acoustic microscope (SAM) and a computer for processing reflected flaw signals to produce enhanced images. Although scanning acoustic microscopes are capable of operating at frequencies of the order of 50 Mhz, the effectiveness of scanning acoustic imaging systems has been limited by the lack of a high speed gated peak detector. There are no available gated peak detectors which operate effectively above about 20 Mhz. Moreover, known gated peak detectors require a number of pulse repetitions (anywhere from 2 to 12, for example, depending upon frequency) for their output to settle to within 5% of the peak value. This necessitates using multiple pulses of a lower than desirable frequency and pulse repetition rate, and significantly increases the scanning and flaw acquisition time.

One approach which has been employed to avoid the frequency limitations of gated peak detectors has been to use a device such as a waveform recorder to increase the waveform time scale and decrease the frequency sufficiently (by a factor of 500, for example) to enable the peak detector to follow the waveform. Typically, samples of the waveform are digitized, stored in a memory, and clocked out at a fixed rate. For a 1 microsecond per word clock rate and a memory having a capacity of 1024 words, the cycle time for full memory readout is approximately 1 millisecond, which sets the system's maximum repetition rate at 1000 pulses per second. Not only does this significantly increase the system scanning and defect acquisition times, such devices add unnecessary expense and complexity to the system.

In addition to their limited frequency and pulse repetition rate, other disadvantages of known gated peak detectors include their limited dynamic range (typically 20 dB), and their inaccuracy in measuring the peak amplitude of a single pulse or an asymmetrical waveform.

It is desirable to provide high speed gated peak detectors which avoid these and other problems of known gated peak detectors, and it is to this end that the present invention is directed.

SUMMARY OF THE INVENTION

Significantly, the invention affords peak detector apparatus having highly advantageous and desirable characteristics. Peak detectors in accordance with the invention can be used with RF signal frequencies of the order of 50 Mhz or greater and with pulse repetition rates of the order of 10,000 pulses per second, can detect accurately the peak amplitude of a single pulse waveform, can detect simultaneously both positive and negative peak amplitudes and automatically output the larger peak amplitude, as well as the peak-to-peak signal amplitude (which is a more realistic indication of flaw size since the reflected waveform is usually asymmetrical), and hold the measured values for one repetition period, and have an analog and digital output with a useful dynamic range of the order of 26 dB.

Briefly stated, in one aspect, peak detector apparatus in accordance with the invention comprises a first detector means for detecting the peak positive value of an input waveform within a preselected period of time and for providing a first signal corresponding to the detected value; second detector means for detecting, within said preselected period of time, the peak negative value of the input waveform and for providing a second signal corresponding to the peak negative value; means responsive to the first and second signals for determining the peak-to-peak value of the waveform and for providing a third signal representative of the peak-to-peak value; means for comparing the first and second signals to detect which signal is the larger; and selector means responsive to the comparing means for providing a fourth signal corresponding to the larger of said first and second signals.

In another aspect, the first and second detector means include high speed operational amplifier peak detectors which are absolutely stable driving a capacitive load, and associated high speed sample and hold circuits which hold the detected positive and negative peak values of the input waveform. The positive and negative peak values are combined to provide a peak-to-peak value, which may be digitized using an analog-to-digital converter to provide a digital output to a computer for image processing. The positive and negative peak values are further compared to detect the larger value, and this value is automatically output as a positive analog signal, thereby avoiding distortion in the peak amplitude determination due to phase shifts in the input signal.

DESCRIPTION OF THE PREFERRED EMBODIMENT

The invention is particularly well adapted for use with scanning acoustic imaging systems for the non-destructive testing of parts, and will be described in that context. However, as will become apparent from the description which follows, the invention has greater utility and may be advantageously employed in other signal processing applications requiring high speed gated peak detection.

Figure 1:
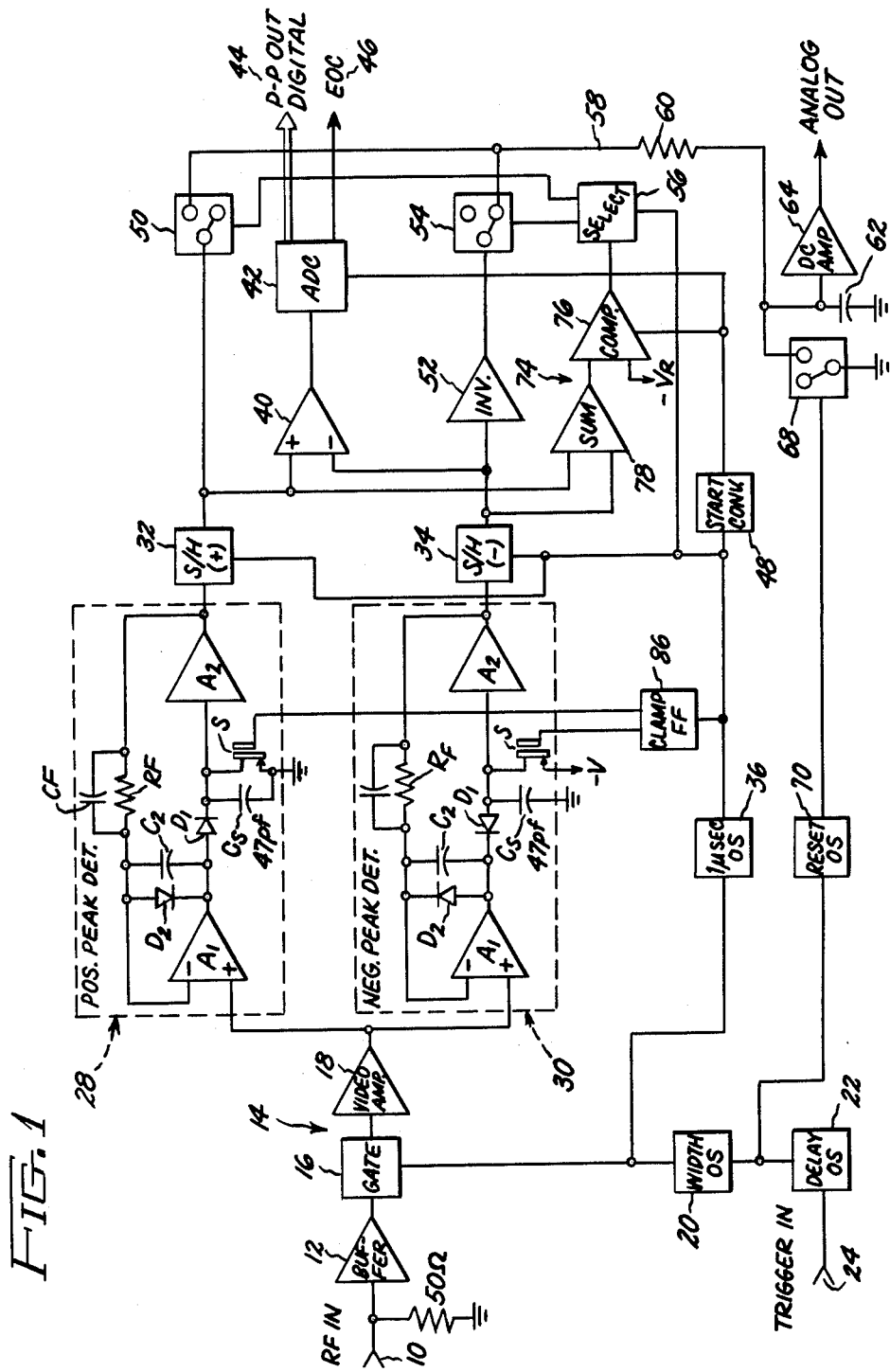
FIG. 1 is a block diagram of gated peak detector apparatus in accordance with the invention.

FIG. 1 is a block diagram of high speed gated peak detector apparatus in accordance with the invention. As shown, an RF signal may be input on a terminal 10, which may be terminated in 50 ohms, to a buffer amplifier 12 and a gated video amplifier 14 comprising a gate 16, which may be a solid state switch preferably having an on/off ratio of greater than 50 dB, and a video amplifier 18 preferably having a 100 Mhz bandwidth. The gate may be controlled by a gate width circuit 20, which may be a one-shot multivibrator, and a gate delay circuit 22, which may also be a one-shot multivibrator, in response to a trigger signal input on a terminal 24. Gate 16 enables the input RF signal to be observed at preselected times and during a preselected time window, as hereinafter described. Video amplifier 18 is employed for increasing the maximum peak linear RF input signal, which may have an amplitude of the order of ±0.6 volts, for example, to a value of the order of ±2.5 volts. The output from the video amplifier is split and applied in parallel to a positive peak detector 28 and to a negative peak detector 30, which will be described in more detail shortly. The output of each peak detector is connected to an associated high speed sample and hold (S/H) circuit 32 and 34, respectively. The S/H circuits may be of conventional design, and preferably have an acquisition time of the order of 1 microsecond. The S/H circuits may be controlled by a one microsecond one-shot 36 connected to the output of gate width circuit 20, as shown. One-shot 36 adds a 1 microsecond delay to the time that the peak detector clamps (to be described) are open, so that the RF signal can occur at any time within the gate and the S/H circuits will have sufficient time to acquire the peak signal amplitude. The voltage droop rate of the S/H circuits may be of the order of 10 microvolts per microsecond, maximum, so that a repetition rate of less than 500 pulses per second would be required to produce an output droop equivalent to one bit. Any faster repetition rate would have a proportionately smaller droop.

The signal amplitude values held in the S/H circuits 32 and 34 correspond, respectively, to the peak positive and the peak negative values of the input RF signal detected by the positive peak detector 28 and the negative peak detector 30 during the time that gate 16 is open. The peak values held in the S/H circuits are applied to a differential amplifier 40, as shown. The analog output signal from the differential amplifier, which preferably has a range of the order of 0 to 5 volts, corresponds to the peak-to-peak amplitude of the RF input signal. This output signal from the differential amplifier is supplied to the input of an analog-to-digital converter (ADC) 42, which may be of conventional design. The ADC digitizes the peak-to-peak analog signal (preferably to an accuracy of 8 bits) and supplies the converted signal to an output 44 as an 8-bit parallel peak-to-peak digital output signal. The conversion time of the ADC is preferably of the order of 4 microseconds, and the completion of conversion may be indicated by an end of conversion (EOC) signal which is output at 46. The peak-to-peak and EOC digital signals may be supplied to a computer for processing. The ADC may be controlled by a start conversion circuit 48, which may comprise a one-shot connected to the one microsecond one-shot 36, as shown, so that the A/D conversion is initiated after the peak detector clamps have closed and the S/H circuits are in their hold state, as described hereinafter.

As is further illustrated in FIG. 1, the positive peak value stored in S/H 32 is also supplied to the input of a switch 50 and the negative peak value stored in S/H 34 may be inverted by an inverter amplifier 52 and supplied to the input of a second switch 54. Switches 50 and 54 may be controlled by a select circuit 56, which may comprise a flip flop, to supply either the positive peak signal or the negative peak signal (inverted by inverter 52) to a common output line 58. Output line 58 may be connected through a resistor 60 to an analog sample and hold circuit, which may comprise simply a grounded capacitor 62 on the input of a DC amplifier 64. The select circuit 56 controls switches 50 and 54 (as will be described shortly) such that the signal supplied to the analog S/H capacitor 62 is the larger (absolute magnitude) of the positive and negative peak values held in S/H circuits 32 and 34. The output from the DC amplifier is an analog signal corresponding to the larger peak value and may be employed for gray scale recording, digital or analog display, or high-low alarms and the like. The analog S/H capacitor 62 may be reset at the start of each gate period by a switch 68 (which shunts the capacitor to ground) controlled by a reset circuit 70, which may comprise a one-shot, connected to the output of gate delay 22.

Select circuit 56 may be controlled by the control signal from one-shot 36 to the S/H circuits and by the output of an automatic polarity selector circuit 74 comprising a comparator 76 and a summing amplifier 78, as shown. The inputs to the summing amplifier are the peak values held in the S/H circuits 32 and 34, and the output of the summing amplifier is connected to one input of the voltage comparator. A second input of the voltage comparator is connected to a negative reference voltage ($-V_R$), as shown. The automatic polarity selector circuit 74 determines which of the peak values held in the S/H circuits is larger, and controls select circuit 56 so as to supply the larger value to the analog S/H capacitor 62. During the time that the detected peak signals are being converted, voltage comparator 76 is controlled by the output of start conversion circuit 48 such that switches 50 and 54 are in the positions illustrated in the figure. This selects the negative S/H 34 output inverted by inverter 52. Thereafter, if the positive S/H 32 output is greater than the negative S/H output (by approximately 10 millivolts), the output of the comparator causes select circuit 56 to select the positive S/H output. Otherwise, the negative S/H output (inverted) remains connected to the analog S/H. In this manner, the apparatus automatically selects and outputs a positive analog signal from the DC amplifier corresponding to the larger of the positive and negative peak values.

Figure 2:
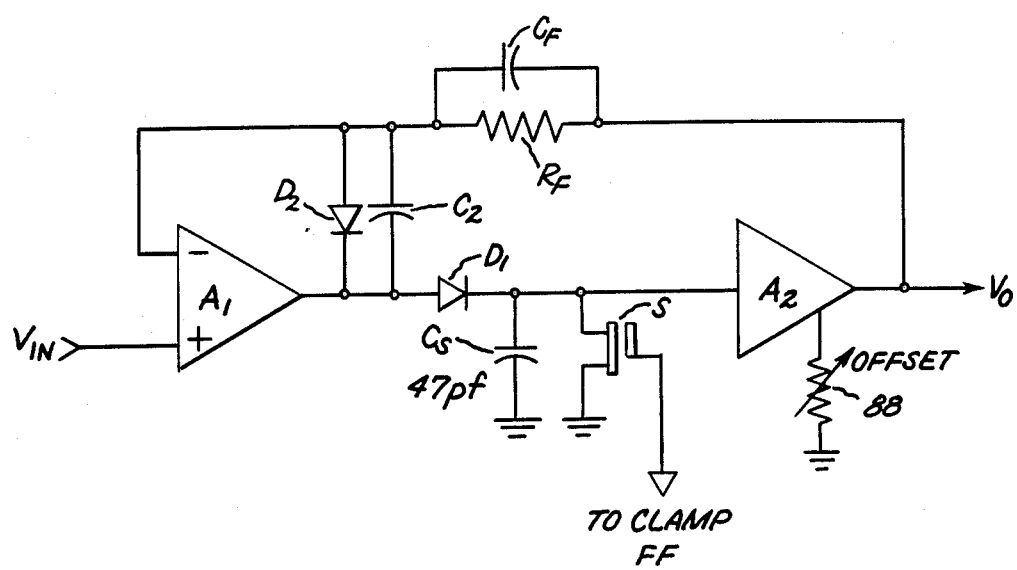
FIG. 2 is a block diagram of a positive peak detector of the apparatus of FIG. 1.

FIG. 2 illustrates the configuration of the positive peak detector 28. The negative peak detector 30 may have a similar configuration, except as noted hereinafter, and like reference designators are employed in the drawings for like elements of the two peak detectors. As shown in FIG. 2, the input voltage $V_{in}$ (from video amplifier 18) is supplied to the positive input of an amplifier $A_1$ connected in a negative feedback configuration. The output of the amplifier is connected through a diode $D_1$ to the input of a second amplifier $A_2$ within the feedback loop. The output voltage $V_o$ of amplifier $A_2$, which corresponds to the peak value of the input signal to the peak detector, is supplied to S/H circuit 32 (see FIG. 1) and is fed back to the negative input of amplifier $A_1$ through a feedback resistor $R_F$ connected in parallel with a capacitor $C_F$. A second diode $D_2$ in parallel with a capacitor $C_2$ may be connected between the negative input and the output of amplifier $A_1$, as shown. Diode $D_2$ prevents amplifer $A_1$ from latching up when the peak is detected breaking the feedback loop. Capacitors $C_F$ and $C_2$ may be selected to stabilize the loop and prevent overshoot for a step input signal. The output of diode $D_1$ is connected to a grounded storage capacitor $C_S$, which may have a value of 47 pf, for example, and capacitor $C_S$ is shunted by a solid state switch S, which is preferably a FET switch, which discharges the capacitor at the beginning of each repetition period. As shown in FIG. 1, switches S of both the positive and negative peak detectors may be controlled by a clamp circuit 86, which may be a flip flop, connected to the output of the 1 microsecond one-shot 36.

Basic peak detection is performed by diode $D_1$ and storage capacitor $C_S$. When the output of amplifier $A_1$ goes positive, capacitor $C_S$ is charged through the diode to the peak value of the positive going signal. When the signal amplitude drops below the value stored in the capacitor, the diode is reverse biased so that the circuit is opened and the peak value is held in the capacitor. If both the diode and the capacitor are perfect (no leakage), then the capacitor can hold the peak amplitude for a long time (assuming the FET switch S has low leakage and the input impedance of amplifier $A_2$ is high). An offset adjustment 88 of amplifier $A_2$ may be set so as to forward bias diode $D_1$ (when capacitor $C_S$ is discharged) to improve the circuit's linearity.

To afford high speed (50 Mhz) response, amplifiers $A_1$ and $A_2$ should be high speed, high bandwidth amplifiers, and amplifier $A_1$ must be stable driving a capacitive load. Amplifier $A_1$ is preferably a Teledyne Philbrick type 1443 operational amplifier, which is a FET input amplifier having a unity gain bandwidth of 80 Mhz, a slew rate of 1000 volts per microsecond, an output voltage swing of $\pm 10$ volts with 100 ma of current, and is absolutely stable driving a 54 picofarad capacitive load, which are ideal characteristics for the gated peak detector. Amplifier $A_2$ is preferably a type LH0033 FET input follower amplifier having a bandwidth of 100 Mhz, and a slew rate of 1500 volts per microsecond. Switch S, which discharges capacitor $C_S$, is preferably a type SD211 FET switch. The diodes are preferably Schottky diodes such as type HP2810, which have a reverse current of the order of 100 nanoamps. This leakage current produces a 1 bit (19.5 millivolts) peak detector voltage droop in 9 microseconds, which is of little consequence since the sample and hold acquisition time is only 1 microsecond.

As shown in FIG. 1, the negative peak detector 30 may be identical to the positive peak detector, except that diodes $D_1$ and $D_2$ are reversed (so that the circuit responds to negative going signals and capacitor $C_S$ charges to the negative peak value), and the source of FET switch S is connected to a negative voltage $(-V)$ which is more negative than the negative peak value to enable the capacitor to be discharged.

In operation, an RF signal on terminal 10 (see FIG. 1) is gated to video amplifier 18 by gate 16 in response to a trigger input signal on terminal 24, the gate opening time and width being determined by delay circuit 22 and width circuit 20, which may be adjustable. The trigger signal may be derived from any convenient source, such as (in ultrasonic testing) the source of the acoustic signal or a reflected signal from the water/part interface. The amplified signal from the video amplifier is applied to the positive and negative peak detectors, which detect the positive and negative peaks of the signal, respectively, during the gate open time. The gate signal from circuit 20 is also applied to the one microsecond one-shot 36, the output of which opens switches S of the peak detectors via the clamp flip flop 86 and actuates the S/H circuits 32 and 34 to acquire the peak positive and negative values.

As noted earlier, the S/H circuits have an acquisition time of one microsecond, and the one microsecond one-shot 36 adds this delay to the time the peak detector clamp is open so that the RF signal can occur at any time within the gate and the S/H circuits will have sufficient time to acquire the peak amplitudes. The start conversion one-shot 48 initiates analog-to-digital conversion of the peak-to-peak signal from amplifier 40 after the peak detector clamps have closed and the S/H circuits are in their hold state. An advantage of using high speed S/H circuits at the outputs of the peak detectors is that the peak detector clamps need only be open for the length of the gate signal plus the acquisition time of the S/H circuits. As noted earlier, analog-to-digital conversion of the peak-to-peak signal from amplifier 40 is accomplished by ADC 42 in four microseconds and is indicated by an end of conversion (EOC) signal, which is useful for computer processing. Reset one-shot 70 resets the analog S/H capacitor 62 at the start of each gate period, and the larger of the peak signals is output as an analog signal from DC amplifier 64.

The use of high speed amplifiers for the peak detectors and high speed S/H and ADC circuits in the peak detector apparatus of the invention results in a total maximum signal processing time of the order of 6.5 microseconds, which is an order of magnitude faster than that required for operation at 10,000 pulses per second. This significantly enhances the scanning speed and effectiveness of a scanning acoustical imaging system employing the peak detector apparatus, since it enables processing in real time of 50 Mhz, 10,000 pulses per second signals.

FIGS. 3A–C and 4A–C illustrate, respectively, the positive peak detector response and the negative peak detector response of the peak detector apparatus of FIG. 1 to a reflected signal from the quartz buffer rod of a 50 Mhz transducer. The figures illustrate the outputs of the peak detectors superimposed on the input signal as measured at the output of the gated video amplifier. As shown, the signal is asymmetrical, with the positive peak amplitude approximately equal to $+2.5$ volts and the negtive peak amplitude approximately equal to $-2.0$ volts.

Figure 3A:
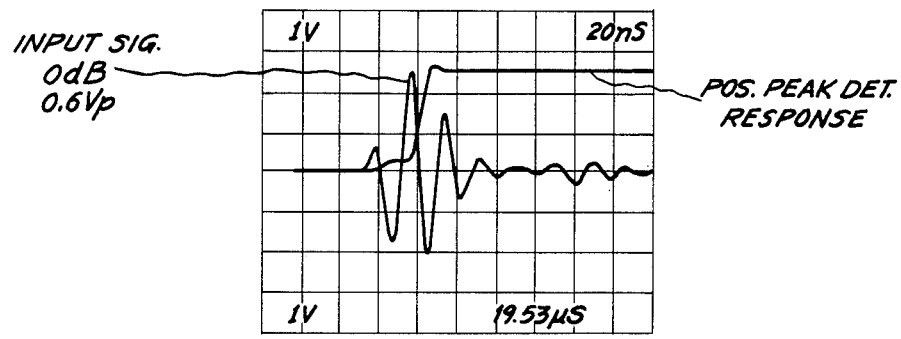
FIGS. 3A–C illustrate the response of the positive peak detector of FIG. 2.
Figure 4A:
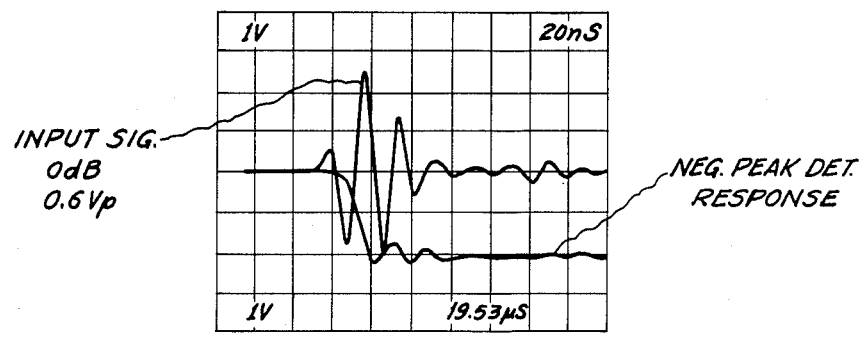
FIGS. 4A–C are similar views to FIGS. 3A–C and illustrate the response of a negative peak detector of the apparatus of FIG. 1.

FIGS. 3A and 4A illustrate the responses for a 0 dB (0.6 volt peak) input signal. The vertical scale is one volt/division and the horizontal scale is 20 nsec/division. The peak detector response is delayed approximately 8 nanoseconds from the actual peak, which corresponds to the propogation delay through amplifiers $A_1$ and $A_2$. FIGS. 3A and 4A clearly show that the peak detector can follow a 50 MHz waveform and detect its peak value.

Figure 3B:
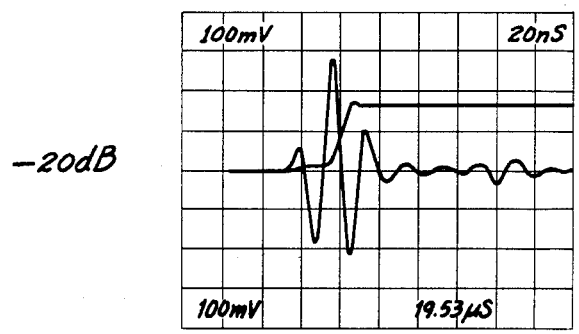
Figure 4B:
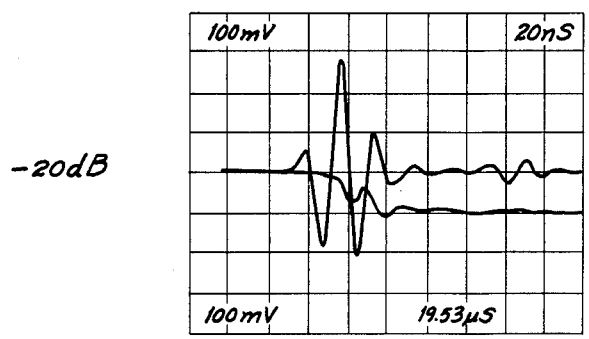

FIGS. 3B and 4B illustrate the peak detector responses when the input signal is reduced by 20 dB. The vertical scale is 100 mV/division, and the horizontal scale is 20 nsec/division. As shown, the peak detector responses are approximately 50% of the peak value. This condition is caused by the increase in forward resistance of diodes $D_1$ (HP2810) for low amplitude signals, and may be improved by increasing the signal amplitude or employing a diode having a lower forward resistance (such as GaAs) and which also has a high reverse resistance. Nevertheless, the dynamic range of the peak detector is 26 dB, which may be improved by replacing the diodes as indicated.

Figure 3C:
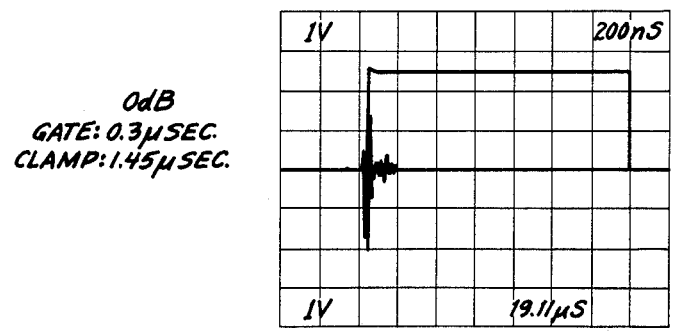
Figure 4C:
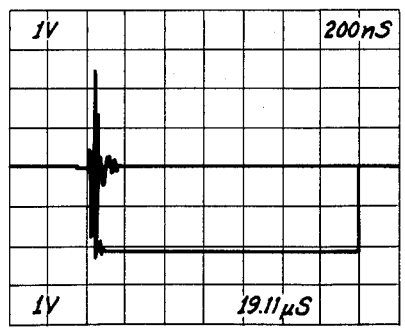

FIGS. 3C and 4C are for a 0 dB input signal, and show the length of time that the peak detector clamps are open. The gate is open for approximately 0.3 microseconds, and the clamps are open for approximately 1.45 microseconds to allow time for the S/H circuits to acquire the peak amplitudes. The analog output signal from DC amplifier 64 is held for the entire repetition period, and would correspond to the value of the positive peak amplitude, since in this case the positive peak amplitude is greater than the negative peak amplitude.

Significantly, the invention needs only one pulse of a 50 Mhz waveform in order to detect its peak amplitude, i.e., settle to within 5% of the peak value. This has been verified by connecting an oscilloscope to the analog output and manually triggering the peak detector. The same amplitude is shown on the scope whether the peak detector is triggered with one pulse or 10,000 pulses per second.

The accuracy of the peak detector output over its dynamic range is illustrated in the following Table. The results were determined in two different ways. First, a scope was employed to measure the outputs of the RF amplifier and the peak detector. Secondly, a pseudo RF peak amplitude based upon the peak RF amplitude indicated on the scope was calculated, but corrected for a 5% reduction due to the reset time/repetition time ratio effect on the DC output as measured by a digital voltmeter (DVM). The Table shows the differences for the two approaches between the amplitude as measured at the RF amplifier and the amplitude of the peak detector output.

TABLE

| INPUT SIGNAL LEVEL (dB) | SCOPE RF AMP (VOLTS) | SCOPE PK DET OUTPUT (VOLTS) | DIFF. (VOLTS) | PSEUDO RF AMP (VOLTS) | DVM PK AMP OUTPUT (VOLTS) | DIFF. (VOLTS) |
|---|---|---|---|---|---|---|
| 0 | 2.5 | 2.5 | 0 | 2.365 | 2.365 | 0 |
| −2 | 2.0 | 2.0 | 0 | 1.892 | 1.919 | +.027 |
| −4 | 1.6 | 1.6 | 0 | 1.514 | 1.511 | −.003 |
| −6 | 1.3 | 1.25 | −.05 | 1.230 | 1.170 | −.06 |
| −8 | 1.0 | 0.90 | −.1 | 0.946 | 0.896 | −.05 |
| −10 | 0.82 | 0.72 | −.1 | 0.776 | 0.687 | −.089 |
| −12 | 0.66 | 0.54 | −.12 | 0.624 | 0.517 | −.107 |
| −14 | 0.52 | 0.40 | −.12 | 0.492 | 0.407 | −.085 |
| −16 | 0.41 | 0.31 | −.1 | 0.388 | 0.325 | −.063 |
| −18 | 0.33 | 0.23 | −.1 | 0.312 | 0.253 | −.059 |
| −20 | 0.27 | 0.16 | −.11 | 0.255 | 0.203 | −.052 |
| −22 | 0.21 | 0.12 | −.09 | 0.199 | 0.170 | −.029 |
| −24 | 0.17 | 0.09 | −.08 | 0.161 | 0.154 | −.007 |
| −26 | 0.13 | 0.07 | −.06 | 0.123 | 0.147 | +.024 |
|  |  |  | 0 |  | 0.142 |  |
|  |  | MAX. −4.8% FS |  |  |  | −4.5% FS |
|  |  |  |  |  |  | +1.1% FS |

The full scale (FS) values are 2.5 volts (scope) or 2.365 volts (DVM). The peak detector output is within approximately −5% of full scale by both measurements over a 26 dB dynamic range. Peak detector linearity is usually specified as a percentage of full scale in order to de-emphasize the larger absolute input/output ratios which typically occur for low amplitude signals.

As will be appreciated from the foregoing, peak detector apparatus in accordance with the invention has a number of significant advantages. It can be used with signal frequencies of the order of 50 Mhz or more and pulse repetition rates as high as 10,000 pulses per second. Moreover, the peak amplitude of a single waveform can be detected, and both positive and negative peak amplitudes are detected simultaneously to afford a peak-to-peak signal amplitude which is digitized and output for computer processing. In addition, the polarity of the larger of the positive and negative peak amplitudes is determined automatically, and this amplitude is provided as an analog output which is held for one repetition period, i.e., gate period. In addition, the peak detector has a useful dynamic range of 26 dB, which exceeds that available with known peak detectors.

While a preferred embodiment of the invention has been shown and described, it will be appreciated by those skilled in the art that changes may be made in this embodiment without departing from the principles and spirit of the invention, the scope of which is defined in the appended claims.

What I claim as new and desire to secure by Letters Patent of the United States is:

1. Peak detector apparatus comprising:

first detector means for detecting the peak positive value of an input waveform within a preselected period of time and for providing a first signal corresponding to the peak positive value;

second detector means for detecting, within said preselected period time, the peak negative value of the input waveform and for providing a second signal corresponding to the peak negative value;

gate means connected to the first and second detector means for supplying the input waveform in parallel to both detector means during said preselected period of time;

means responsive to the first and second signals for determining the peak-to-peak value of the waveform and for providing a third signal representative of the peak-to-peak value;

means for comparing the first and second signals to detect which signal is the larger; and selector means responsive to the comparing means for providing a fourth signal corresponding to the larger of said first and second signals.

2. The apparatus of claim 1 further comprising means for controlling the times at which the gate means opens and the duration of time that the gate means is opened, said duration of time corresponding to said preselected period of time.

3. The apparatus of claim 1, wherein said first and second detector means each comprise a peak detector for detecting said peak value and a sample and hold circuit connected to the peak detector for sampling the detected peak value and for holding said sampled value for a predetermined time.

4. The apparatus of claim 3, wherein said peak detector comprises an amplifier for receiving the input waveform, a diode having an input connected to an output of the amplifier, a capacitor which charges to the peak value of the input waveform during said preselected period of time connected to an output of the diode, and means for discharging said capacitor after another preselected period of time.

5. The apparatus of claim 4 further comprising another amplifier connected to the output of the diode, the other amplifier having an output connected to the sample and hold circuit and to an input of the first-mentioned amplifier so as to form a feedback configuration.

6. The apparatus of claim 1, wherein said peak-to-peak value determining means comprises a differential amplifier which combines said first and second signals.

7. The apparatus of claim 6 further comprising an analog-to-digital converter connected to said differential amplifier for providing said third signal, the third signal being a digital signal representative of the peak-to-peak value.

8. The apparatus of claim 1, wherein the selector means comprises switch means receiving said first and second signals, a summing amplifier for summing the first and second signals, a comparator for comparing the sum of the first and second signals to a predetermined reference value to detect the larger of the first and second signals, and means responsive to the comparison for controlling the switch means to select the larger of the first and second signals.

9. The apparatus of claim 8 further comprising analog sample and hold means for receiving said larger signal from the switch means and for providing an analog output corresponding thereto, said analog output comprising said fourth signal.

10. The apparatus of claim 9, wherein said input waveform comprises a plurality of pulses having a predetermined repetition period, and wherein said analog sample and hold means comprises a capacitor connected to the input of an amplifier, the output of the amplifier providing said fourth signal, and a switch connected across the capacitor for discharging the capacitor at the beginning of each repetition period.

11. Peak detector apparatus comprising:
a first peak detector for detecting the peak positive value of an input waveform within a first preselected period of time;
a second peak detector in parallel with the foregoing for detecting the peak negative value of said input waveform within said preselected period of time;
first and second sample and hold circuits connected to the first and second peak detectors, respectively, for sampling the detected peak values and for holding the sampled values for a second preselected period of time;
first means connected to the first and second sample and hold circuits and responsive to the sampled values for providing a first output signal corresponding to the peak-to-peak value of the input waveform during said first preselected period of time; and
second means connected to the first and second sample and hold circuits for determining which of the sampled values has the larger magnitude and for providing a second output signal corresponding to the peak value of a selected one of said sampled values having such larger magnitude.

12. The apparatus of claim 11, wherein said determining means comprises a summing amplifier for summing the values held in said sample and hold circuits, a comparator for comparing the sum to a predetermined reference voltage, an inverter amplifier for inverting the sampled value held in the second sample and hold circuit, switch means receiving the sampled value held in the first sample and hold circuit and the inverted value from the inverter, and means responsive to the comparator for controlling the switch means so as to select said sampled value having the larger magnitude.

13. The apparatus of claim 11, wherein said first means comprises a differential amplifier connected to the first and second sample and hold circuits, and an analog-to-digital converter connected to an output of the differential amplifier, said first output signal corresponding to an output from the analog-to-digital converter.

14. The apparatus of claim 11 further comprising a gated amplifier for receiving the input waveform and for providing the input waveform to the first and second peak detectors during said first preselected period of time, and means for controlling the gated amplifier so as to control said first preselected period of time.

15. The apparatus of claim 14, wherein said controlling means comprises a gate width circuit responsive to a trigger signal input to the apparatus for opening said gated amplifier for a time duration corresponding to said first preselected period of time.

16. The apparatus of claim 15, wherein each peak detector comprises a first amplifier receiving said input waveform and having an output connected to an input of a diode so as to pass signals of a predetermined polarity, the diode having an output connected to a capacitor which charges to a peak value of the input waveform during the first preselected period of time and connected to an input of a second amplifier, the second amplifier having an output connected to a corresponding one of said sample and hold circuits and to an input of the first amplifier, and switch means connected across said capacitor for discharging the capacitor after a third preselected period of time.

17. The apparatus of claim 17, wherein said switch means comprises a solid state switch controlled by another controlling means connected to said first-mentioned controlling means, said other controlling means controlling said third preselected period of time.

18. The apparatus of claim 17, wherein said output of the second amplifier is connected to the input of the first amplifier through a feedback circuit, and wherein said feedback circuit includes another diode connected between the input and the output of the first amplifier.

19. The apparatus of caim 11, wherein said input waveform has an asymmetrical polarity and comprises one of a plurality of RF pulses having a pulse repetition rate of the order of 10,000 pulses per second and having a frequency of the order of 50 Mhz.

20. The apparatus of claim 19, wherein said pulses are produced by a scanning acoustic imaging system.

* * * * *